Figure 2:
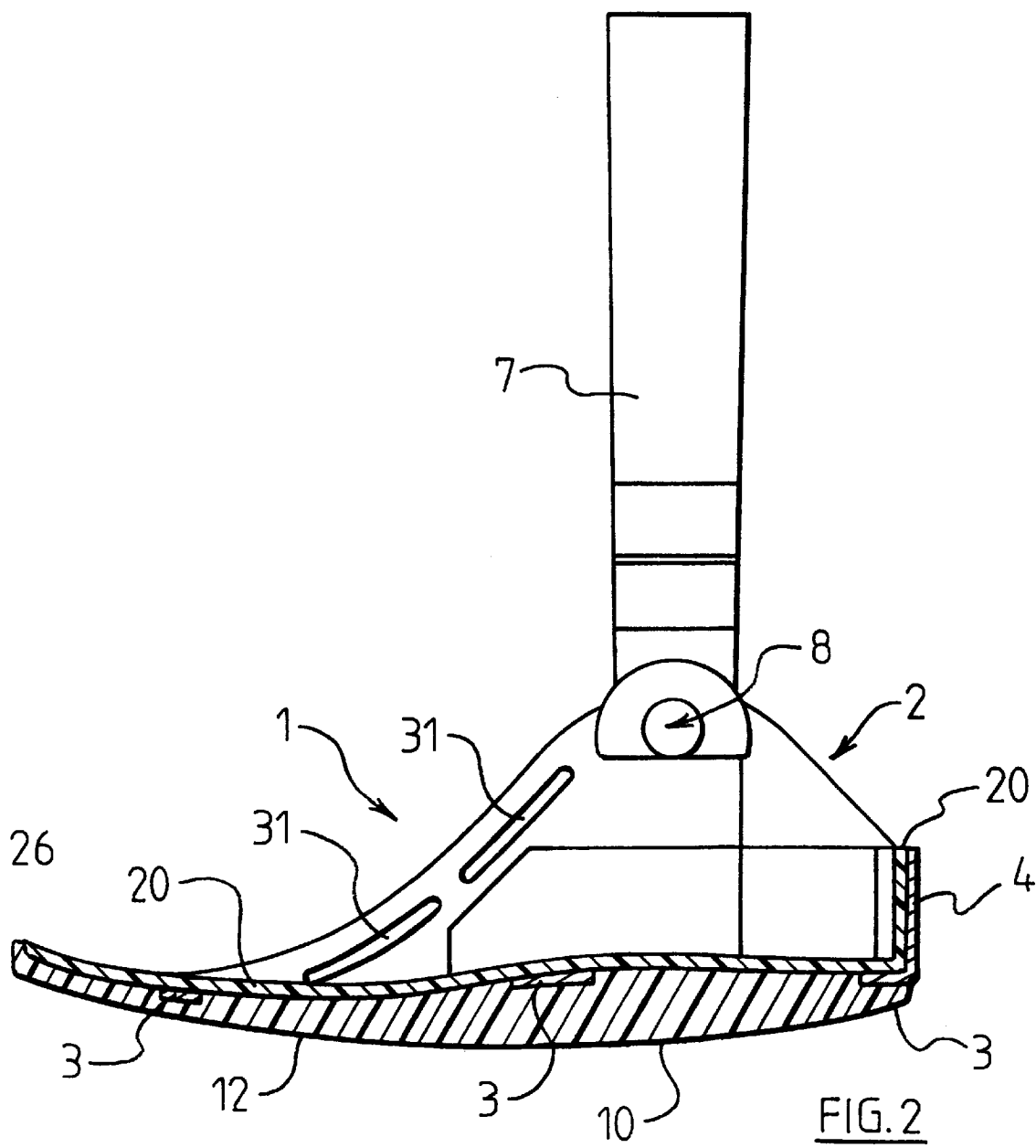

United States Patent [19]
Gilmour

[11] Patent Number: 5,954,075
[45] Date of Patent: Sep. 21, 1999

[54] WALKER

[75] Inventor: Robert Farrer Gilmour, Auckland, New Zealand

[73] Assignee: Bodyworks Healthcare Limited, Auckland, New Zealand

[21] Appl. No.: 08/984,655

[22] Filed: Dec. 3, 1997

[51] Int. Cl.⁶ .................................................. A61H 3/00
[52] U.S. Cl. ............................. 135/84; 135/65; 135/67; 135/82; 135/86
[58] Field of Search .................................. 135/67, 77, 78, 135/84, 86, 65, 82; 248/188.8, 188.9; 182/108, 111

[56] References Cited

U.S. PATENT DOCUMENTS

| | | | |
|---|---|---|---|
| 2,005,507 | 6/1935 | Russell et al. | 135/65 |
| 2,264,570 | 12/1941 | Holden | 135/84 X |
| 4,274,430 | 6/1981 | Schaaf et al. | 135/65 |
| 4,884,587 | 12/1989 | Mungons | 135/65 |
| 5,370,203 | 12/1994 | Kiska | 182/111 |
| 5,865,203 | 2/1999 | Villano | 135/65 |

*Primary Examiner*—Robert Canfield
*Attorney, Agent, or Firm*—Young & Thompson

[57] ABSTRACT

The walker of the invention comprises a chassis including a bottom plate. A sole is engaged or engageable with the underside in use of the bottom plate and a liner is placed within the chassis. The movement characteristics of the walker being determined by the shape or configuration of the sole, or both the shape and configuration.

8 Claims, 5 Drawing Sheets

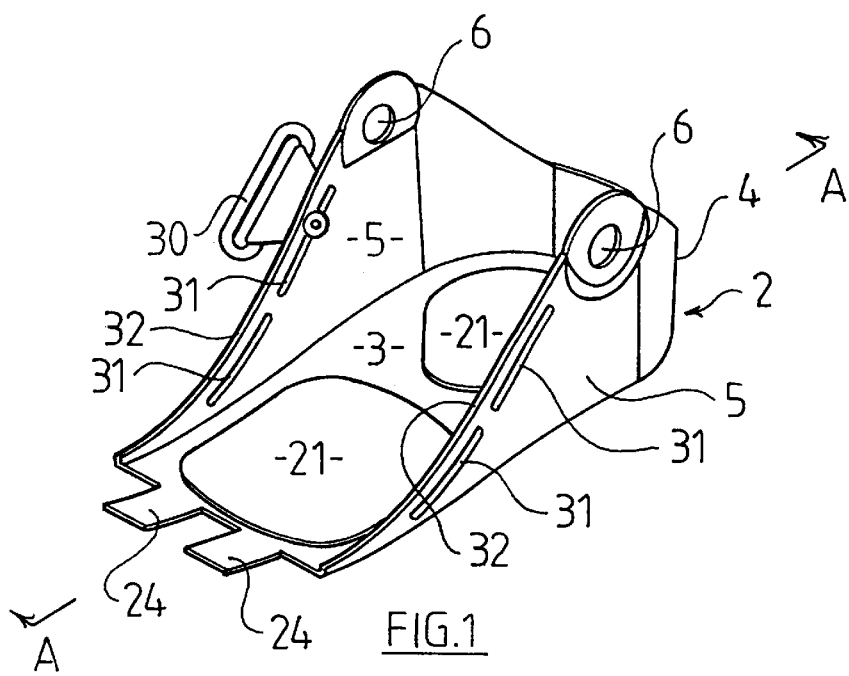
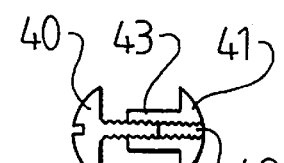

WALKER

This invention relates to a walker particularly to an orthotic walker.

Orthotic walkers at present available have some disadvantages. An orthotic walker comprises a chassis which is of a size selected from a range of available sizes. In order to provide desired walking characteristics the bottom surface of the walker is shaped and configured so as to give those desired walking characteristics. The walker is finished by providing a thin sole on the underside of the chassis and usually a relatively thin liner is provided on the inside of the chassis. Thus to meet expected requirements for different users a range of sizes of chassis must be provided. This leads to the requirement for suppliers to carry a substantially inventory.

A further disadvantage of such constructions is that the liner must absorb substantially all shocks to the user's foot during movement and this gives rise to lateral shear which is both unpleasant and can traumatise the user. Also the lateral shear can destabilise fractures at the operative site.

It is therefore an object of the present invention to provide a walker and/or a method of forming a walker which will obviate or minimise the foregoing disadvantages in a simple yet effective manner or which will at least provide the public with a useful choice.

Accordingly in one aspect the invention consists in a walker comprising a chassis including a bottom plate, a sole engaged or engageable with the underside in use of the bottom plate, and a liner within the chassis, the movement characteristics of the walker being determined by the shape or configuration of the sole or both.

Preferably the bottom plate is substantially flat.

Preferably the thickness of the liner determines at least in part the size of foot to be accommodated by the chassis.

Preferably the sole is moulded in one piece.

Preferably the liner is moulded in one piece.

Preferably the bottom plate is apertured and the sole is engaged with the bottom plate by direct connection between the sole and the liner through the apertures in the bottom plate.

In a further aspect the invention consists in a method of forming a walker comprising providing a chassis with a bottom plate, engaging a sole to the bottom plate, the sole being shaped or configured or both to determine at least in part the walking characteristics of the walker, and inserting a selected liner into the chassis, Preferably the chassis has one or more apertures in the bottom plate thereof and the liner and the sole are connected directly one to the other through the apertures.

Preferably said method further includes the step of selecting one of a range of available liners to at least in part determine the size of foot to be accommodated in the walker.

Preferably said method further includes a step of moulding the chassis in a suitable tool.

Preferably said method further in step includes the step of inserting or withdrawing inserts into or from the tool to vary the length of the chassis.

Figure 3:
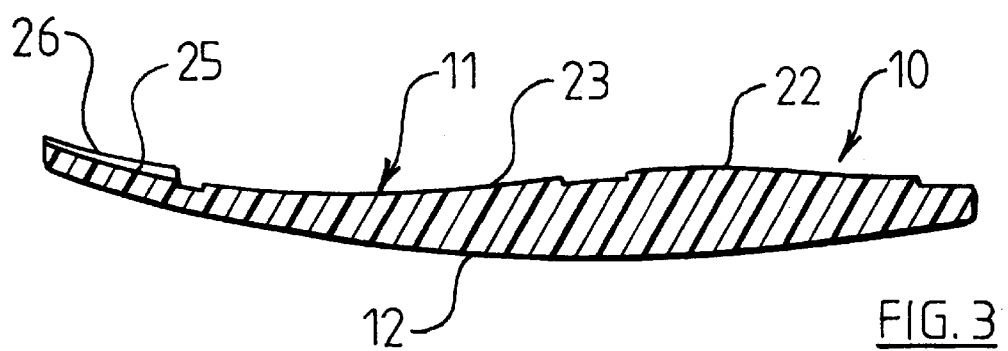
Figure 4:
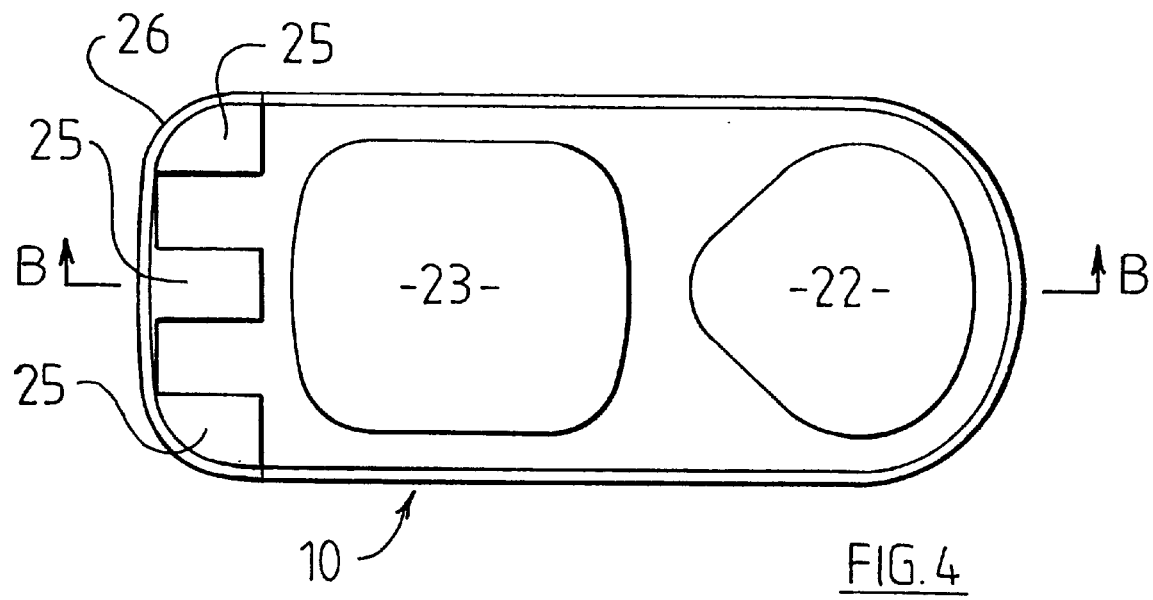
Figure 5:
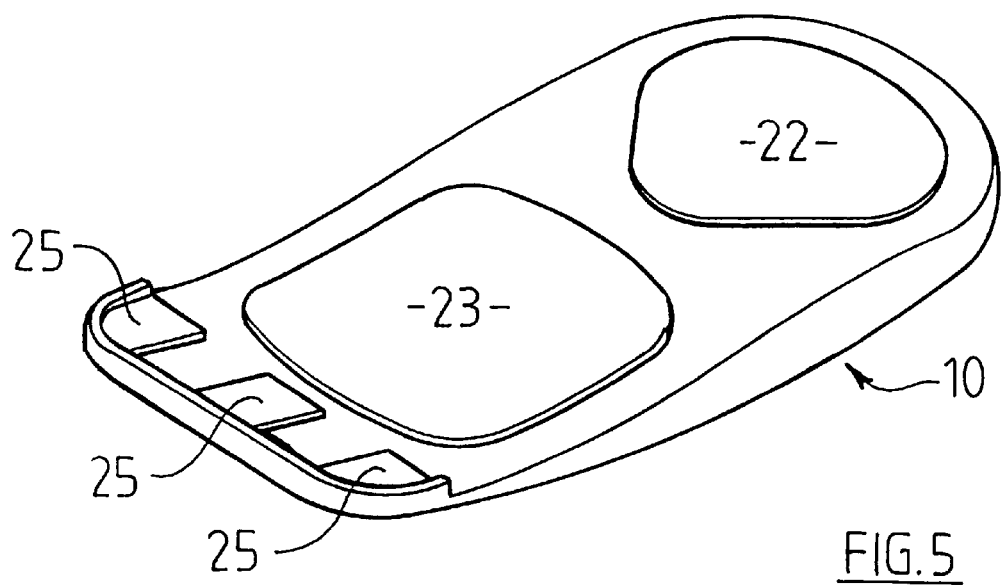
Figure 7:
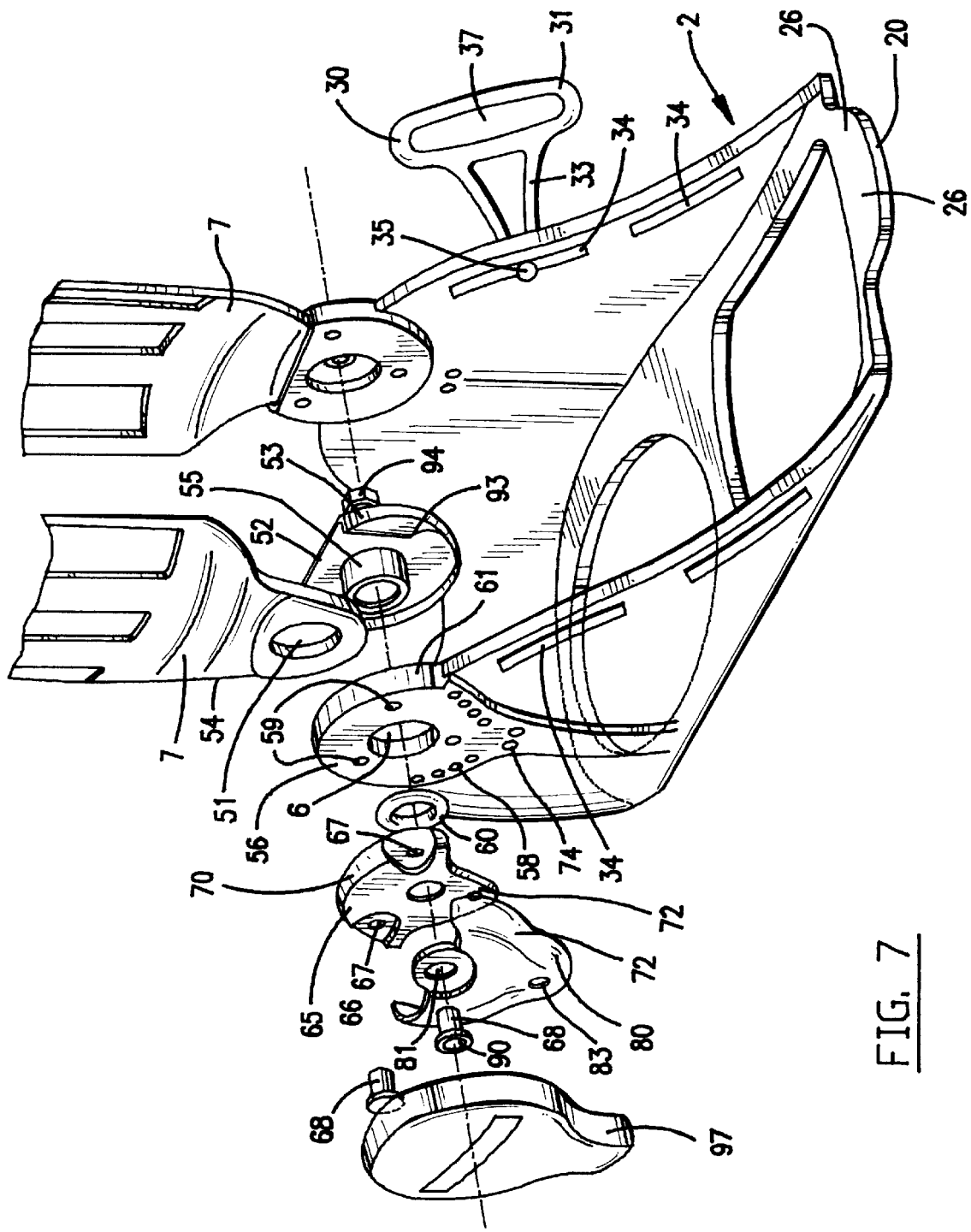
Figure 8:
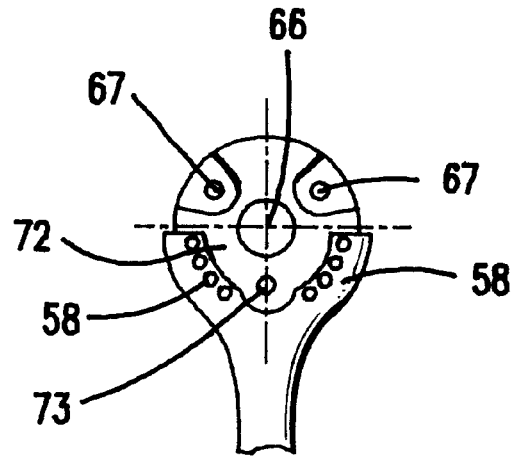

To those skilled in the art to which the invention relates, many changes in construction and widely differing embodiments and applications of the invention will suggest themselves without departing from the scope of the invention as defined in the appended claims. The disclosures and the description herein are purely illustrative and are not intended to be in any sense limiting One preferred form of the invention will now be described with reference to the accompanying drawings in which:

FIG. 1: is a perspective view of a chassis according to one preferred form of the invention, FIG. 2: is a cross-sectional view on A—A in FIG. 1 but further including arms connected to the chassis of FIG. 1, FIG. 3: is a cross-section of a sole according to one preferred form of the invention and being a cross-section on B—B in FIG. 4, FIG. 4: is a plan view of a sole according to one preferred form of the invention, FIG. 5: is a perspective view of the sole of FIGS. 3 and 4, FIG. 6: is a diagrammatic cross-sectional view of a screw used to connect a strap attachment to the chassis of FIG. 1. The chassis of FIG. 1 shows only one such attachment but in practice two or more preferably such attachments would be provided on the chassis, FIG. 7: is a perspective view of an alternative walker chassis showing an "exploded" range of motion device, FIG. 8: is a front elevation of part of the range of motion device of FIG. 7, and FIG. 9: is a diagrammatic view of a possible chafe to use with the chassis of FIGS. 1 or 7.

Referring to the drawings a walker 1 is provided which comprises a chassis 2 which includes a bottom plate 3. The bottom plate 3 may be upturned at the rear edge to provide a back heel plate 4 and also side plates 5 are provided extending upwardly from the bottom plate 3 The side plate 5 carry attachment points 6 so that arms 7 can be attached to the chassis through a suitable range of motion hinge 8.

The attachment points at 6 may comprise suitable apertures through which the range of motion hinge may pass and be secured.

A sole 10 is provided formed of a suitably hard wearing but stiffly resilient material such as a suitable plastics or rubber material and the sole has an upper surface 11 and a lower surface 12. The lower surface 12 is shaped and configured so as to provide the desired walking or motion characteristics of the walker. Thus for example in FIG. 3 the lower surface 12 has a substantial front to back convex curve.

The upper surface 11 is generally shaped to correspond with the lower surface of the chassis 3 and in the preferred embodiment of the invention is substantially flat. As can be seen from the drawings the bottom plate 3 is not flat but is given some shape but still is substantially flatter than the bottom surface 12 of the sole as can be seen by the variation in thickness of the sole 10. Sole 10 is connected to the chassis in a manner to be described further hereinafter.

Within the chassis is provided a liner 20. The liner 20 is similar in shape and configuration to the chassis 2 so as to provide a liner at least where the foot of a user would otherwise contact the chassis 2. The liner 20 is formed from a suitable stiffly resilient material such as a suitable plastics or rubber material. Liners 20 are provided in a range of thicknesses so that the size of foot to be accommodated in the walker is determined at least in part by the thickness of the liner 20. It is envisaged that about three different thicknesses of liner 20 would be provided. The number and thickness of liners are empirically determined.

The sole 10 is desirably connected to the liner 20 by providing cut outs 21 in the bottom plate 3 of the chassis. As can be seen in FIG. 1 the cut outs 21 are of substantial size and in particular are positioned under the heel and ball of the users foot. The sole 10 and liner 20 are directly connected one to the other for example by means of a suitable adhesive where one or the other of the liner 20 and sole 10 passes through the apertures 21. This may be achieved by providing raised portions 22 and 23 on the sole which correspond in size to the cut outs 21 so as to be positioned snugly therein to, the raised portions 22 and 23 being of a height substantially equal to the thickness of the bottom plate 2 so that the upper surface of the sole lies substantially contiguous the lower surface of the liner in the areas of the cut outs 21.

The front of the sole 10 may be located by providing outwardly extending protrusions 24 on the chassis, therebeing two such protrusions shown in FIG. 1. The sole has raised portions 25 and the protrusions 24 are positioned between the raised portions 25. To obtain a correct positioning of the liner 20 a peripheral rib 26 may be provided at least at the toe of the sole so that the liner 20 can become positioned adjacent the rib 26 thereby correctly locating the liner in position to the sole.

It is envisaged that the length of the chassis could be varied by moulding the chassis out of a suitably strong plastics material in a suitable tool. By positioning inserts in the front of the tool the length of the chassis can be varied. It is envisaged that about three chassis lengths would be provided.

In the side plates 5 attachments are provided so that chafe rings can be mounted for the securing straps of the walker. One such ring 30 is shown in FIG. 1 It is envisaged that the mounting would be by means of slots 31 provided in the body of the chassis adjacent a sloped leading edge 32 of the side plates 5. In order to secure the rings 30 a screw of the type shown in FIG. 6 could be used, often known as a Chicago screw, which has a male part 40 substantially in the form of a typical screw and a female part 41 with a threaded aperture 42 therein so that when the part 40 is tightly screwed against the part 41 the shank 43 will still allow the ring 30 to swivel and the screw to move in the slot 31.

One or more, preferably a pair, of arms 7 are engaged with the chassis 2 and this is through the suitable range of motion device.

To this end the arm 7 at its lower end has an aperture 50.

An inner plate 52 is provided which has a peripheral rib 53 open at the top end so that the arm may pass out past the rib in the region 54 of the arm 7.

Extending inwardly is a shaft 55 having a central bore. The shaft 55 passes through the aperture 50 in the arm 50 and also through the aperture 6 in a protrusion 56 carried by the chassis 2. Construction is such that the inner plate 52 moves with the arm 7.

The shaft 55 passes completely through the central aperture 6 and mounts a washer 60. The protrusion carries a pair of apertures 59 the use of which will be described later hereinafter and also beneath the protrusion is provided two sets of apertures 58 through which range of motion pins may be inserted in a desired one of the selected positions, A first outer plate 65 is provided which has a peripheral rim 70 which fits against the outer edge of the protrusion 71. Pins 68 pass through apertures 67 in the outer plate and into the apertures 59 to secure the outer plate to the protrusion 56. A central apertures 56 is provided in the outer plate 65 which also has a downwardly depending portion 72 with an aperture 73 therein.

A second outer plate 80 is provided which has a similar downwardly depending part into which is provided an aperture 83 so that a pin may pass through the aperture 83 the aperture 73 and a suitable one of apertures 74 provided in the frame. A central aperture 81 is also provided in the outer cover through with a which a pin 90 is provided which passes through the aperture 81 the aperture 66 and into the shaft 65 to be secured by nut 94 which is desirably trapped within the inner parts of the shaft 55.

An outer cover 97 is provided to cover the whole mechanism.

The second outer plate 68 also has a peripheral rim 82 to make a suitably positioned fit over the inner plate 65.

In use the outer cover 97 is removed and the pins (not shown) in selected apertures 48 are desirably positioned.

The inner plate 52 is shaped to provide a pair of shoulders 98 which as they rotate strike against the pins in the apertures 48. Therefore by suitably positioning the pins in the apertures 48 the range of motion may be varied.

In use the range of motion pins in the apertures 58 are shifted as desired by removing the final outer cover 97.

A chafe 100 is provided which has a mounting part 102 a strap engaging part 107 and a link part 103. The chafe is desirably formed of a flexible and preferably resilient material such as for example a suitable grade of polyurethane although other materials can be used. The aperture 31 are provided through which the chafe 100 may be engaged with the frame for example by a fixing pin as described with reference to FIG. 6. The slots may be replaced by single apertures if desired.

Figure 9:
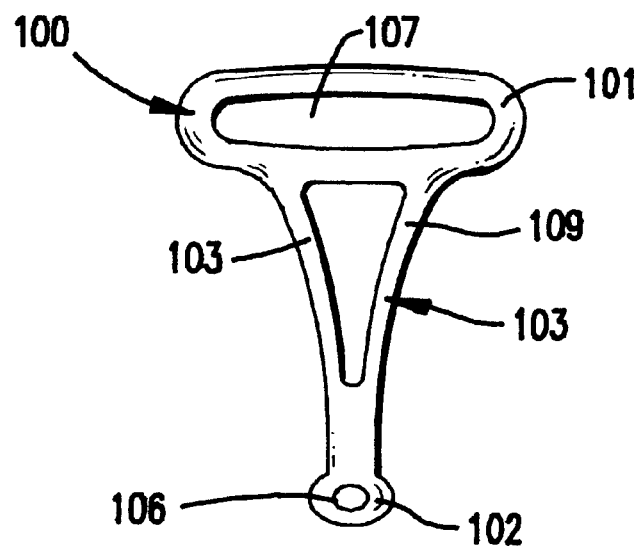

An elongated aperture 31 is provided at the fixing or apertured part through which a strap may be positioned. FIGS. 1 and 6 are shown with a single chafe but of course a pair of chafes on opposite sides of the frame or four chafes can be provided to be secured by a strap interconnected by example by hook and loop pad constructions such as that sold by reference by the trade mark VELCRO. The link part 103 of the chafe is preferably formed by a pair of arms 108 and 109 as can be seen in FIG. 9.

Because of the flexible nature of the chafe in use it will conform to the shape of the users foot by bending and twisting as necessary. This is aided by the provision of the two flexible arms.

The close fit increases the comfort for the user and also aids in providing a suitable tight engagement of the frame to the wearers foot.

In use a walker is fabricated from a chassis and selected sole and liner from the available range. The sole is placed against the underside of the bottom plate 3 and the liner within the chassis with the forward edges of the liner adjacent the rib 26. The sole 10 and liner 20 are then adhered one to the other. The walking characteristics of the walker will be determined by the characteristics of the bottom surface of the sole and the size of foot to be accommodated will be substantially determined by the thickness of the liner selected. If desired a suitable toe cap can be provided for example to clip on to the chassis to provide protection for example in snow or rain. The construction allows wedges such as heel wedges to be inserted, for example, between the chassis and the sole to achieve desired walking characteristics.

Thus it can be seen that at least in a preferred form the walker has a number of advantages. In particular the sole determines the characteristics of the walker rather than the chassis and therefore a range of soles are provided rather than a range of walkers. A single or abbreviated range of chassis are all that need be provided with a range of liners and a range of soles giving a wide variation in available walkers. Different soles and liners can be different colours. In particular the rocking action required is created by the sole. In one form of the invention a single tool can provide different lengths of chassis in a simple manner. The provision of the cut outs and the direct connection of the sole to the liner reduces shock in use and dispersed shock absorption characteristics is advantageous. The use of the screw in the form shown in FIG. 6 allows the position of the tie down straps to be varied over a range of positions. This is desirable as because of bandages or the anatomy of the foot the most desirable position for the tie down straps may change from person to person. Also it is possible to move the tie down straps away from an operative site. The lack of a rigid structure between the heel and the ground allows in time a heel cup to form to increase the stability of the walker for the user.

What we claim is:

1. A walker comprising:

a chassis adapted to accommodate a foot therein, said chassis including a bottom plate;

a sole engaged with the underside of the bottom plate; and a liner within the chassis, the movement characteristics of the walker being determined by at least one of the shape and configuration of the sole.

2. A walker as claimed in claim 1 wherein the bottom plate is substantially flat.

3. A walker as claimed in claim 1 wherein the thickness of the liner determines at least in part the size of foot to be accommodated by the chassis.

4. A walker as claimed in claim 1 wherein the sole is moulded in one piece.

5. A walker as claimed in claim 1 wherein the liner is moulded in one piece.

6. A walker as claimed in claim 1 wherein the bottom plate is apertured and the sole is engaged with the bottom plate by direct connection between the sole and the liner through the apertures in the bottom plate.

7. A walker as claimed in claim 1 wherein the walker further includes one or more arms, each arm being connected to the chassis through a range of motion device.

8. A walker as claimed in claim 1 including at least one flexibly resilient chafe attached to the chassis.

* * * * *

UNITED STATES PATENT AND TRADEMARK OFFICE
CERTIFICATE OF CORRECTION

PATENT NO. : 5,954,075
DATED : September 21, 1999
INVENTOR(S) : Robert Farrer GILMOUR It is certified that error appears in the above-indentified patent and that said Letters Patent is hereby corrected as shown below:

On the title page, insert Item [30] as follows:

--[30]   Foreign Application Priority Data

December 3, 1996    [NZ]    New Zealand........299868--.

Signed and Sealed this

Fifth Day of December, 2000

Attest:

Q. TODD DICKINSON

Attesting Officer

Director of Patents and Trademarks